United States Patent [19]
Halili et al.

[11] Patent Number: 5,586,553
[45] Date of Patent: Dec. 24, 1996

[54] TRANSCUTANEOUS SENSOR INSERTION SET

[75] Inventors: Edgardo C. Halili, Reseda; John J. Mastrototaro, Los Angeles, both of Calif.

[73] Assignee: MiniMed Inc., Sylmar, Calif.

[21] Appl. No.: 393,148

[22] Filed: Feb. 16, 1995

[51] Int. Cl.$^6$ ........................................... A61B 5/05
[52] U.S. Cl. ................. 128/635; 128/637; 128/634; 128/642
[58] Field of Search ..................... 128/632, 634, 128/635, 637, 639–642, 644, 917, 919, DIG. 26; 604/49, 51, 52, 174, 180, 158, 160–164

[56] References Cited

U.S. PATENT DOCUMENTS

| | | |
|---|---|---|
| 3,399,674 | 9/1968 | Pannier et al. . |
| 3,682,173 | 8/1972 | Center .................. 604/160 X |
| 3,878,830 | 4/1975 | Bicher . |
| 4,141,365 | 2/1979 | Fischeli et al. . |
| 4,562,751 | 1/1986 | Nason et al. . |
| 4,573,994 | 3/1986 | Fischell et al. . |
| 4,678,408 | 7/1987 | Nason et al. . |
| 4,685,903 | 8/1987 | Cable et al. . |
| 4,805,625 | 2/1989 | Wyler .................. 604/160 X |
| 4,883,053 | 11/1989 | Simon ................. 604/180 X |
| 4,953,552 | 9/1990 | DeMarzo . |
| 5,071,408 | 12/1991 | Ahmed . |
| 5,108,819 | 4/1992 | Heller et al. . |
| 5,299,571 | 4/1994 | Mastrototaro . |
| 5,390,671 | 2/1995 | Lord et al. .............. 128/635 |

*Primary Examiner*—Angela D. Sykes
*Assistant Examiner*—Samuel Gilbert
*Attorney, Agent, or Firm*—Kelly Bauersfeld & Lowry

[57] ABSTRACT

An insertion set is provided for transcutaneous placement of a sensor such as a glucose sensor at a selected site within the body of a patient. The insertion set comprises a slotted insertion needle extending through a mounting base adapted for mounting onto the patient's skin. A flexible thin film sensor includes a proximal segment carried by the mounting base and defining conductive contacts adapted for electrical connection to a suitable monitor, and a distal segment protruding from the mounting base with sensor electrodes for transcutaneous placement. The distal segment of the sensor extends within a protective cannula, a portion of which is slidably disposed within the insertion needle. Placement of the mounting base onto the patient's skin causes the insertion needle to pierce the skin for transcutaneous placement of the cannula with the sensor therein. The insertion needle can then be withdrawn to leave the cannula and sensor at the selected insertion position, with the sensor electrodes being exposed to patient blood or other extracellular fluid via a window formed in the cannula.

21 Claims, 1 Drawing Sheet

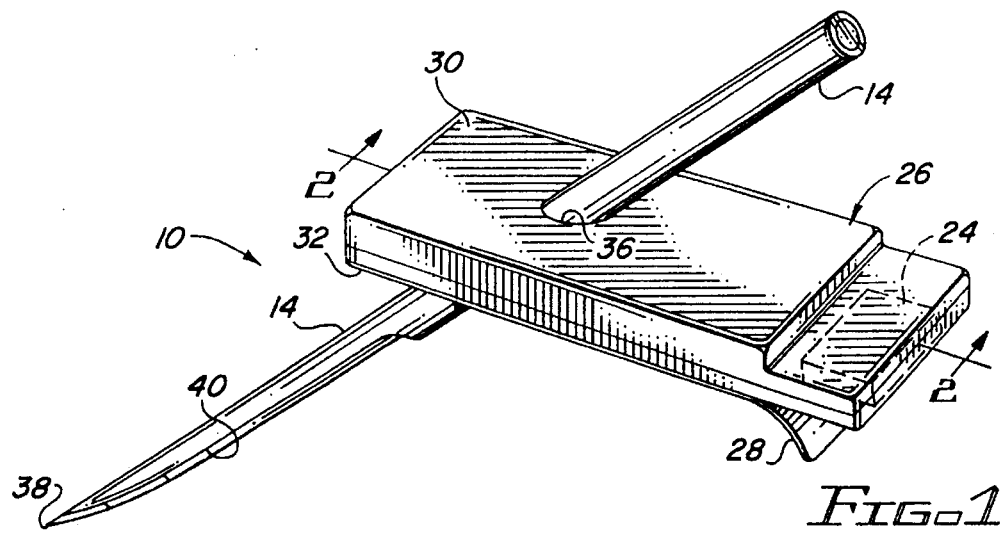
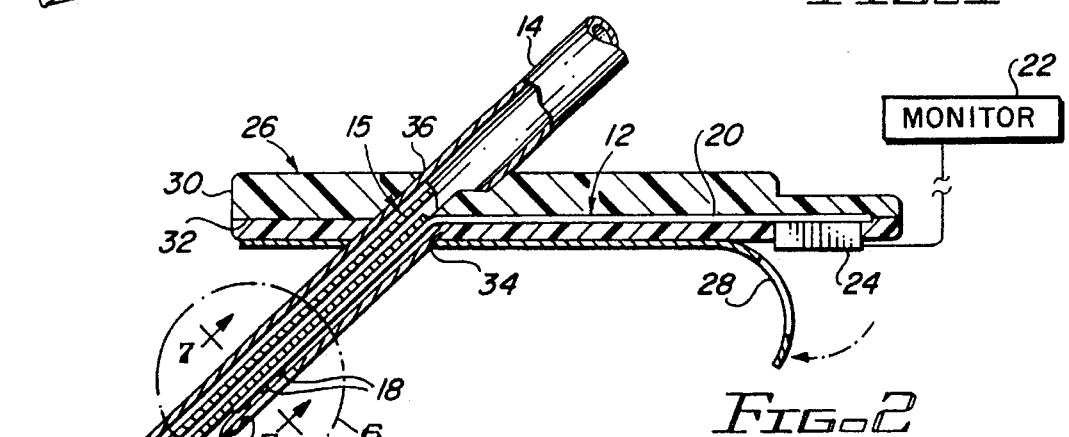
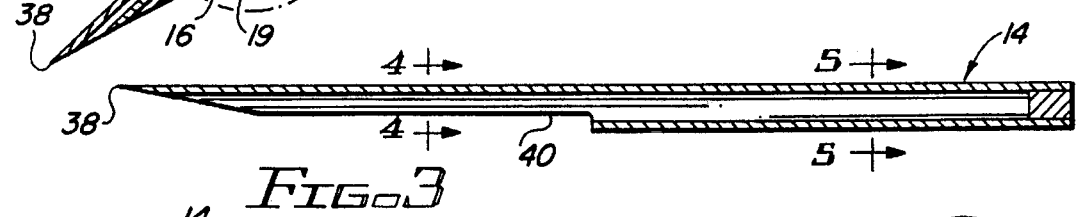
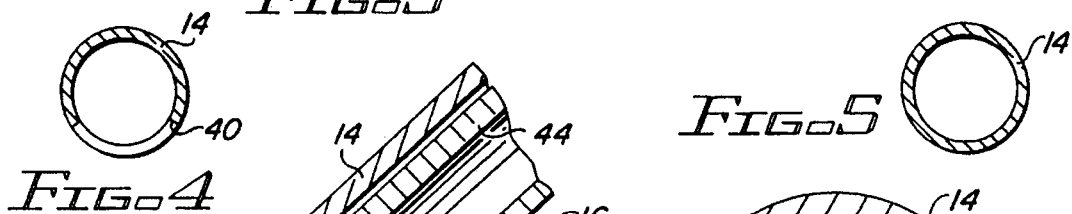
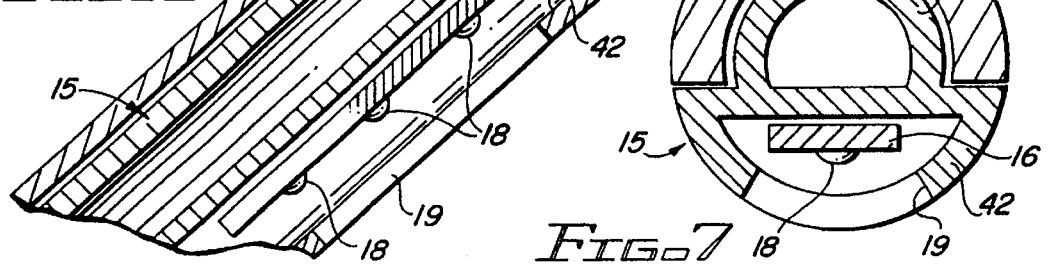
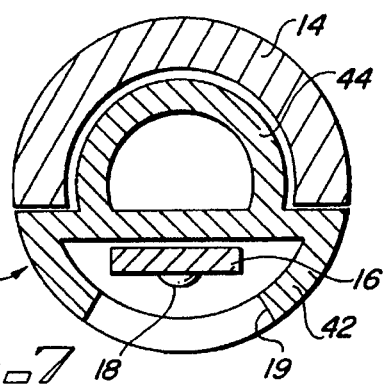

TRANSCUTANEOUS SENSOR INSERTION SET

BACKGROUND OF THE INVENTION

This invention relates generally to devices and methods for placing a sensor at a selected site within the body of a patient. More specifically, this invention relates to an improved and relatively simple insertion set for quick and easy transcutaneous placement of a flexible thin film sensor of the type used, for example, to obtain periodic blood glucose readings.

In recent years, a variety of electrochemical sensors have been developed for a range of applications, including medical applications for detecting and/or quantifying specific agents in a patient's blood. As one example, glucose sensors have been developed for use in obtaining an indication of blood glucose levels in a diabetic patient. Such readings can be especially useful in monitoring and/or adjusting a treatment regimen which typically includes regular administration of insulin to the patient. In this regard, blood glucose readings are particularly useful in conjunction with semiautomated medication infusion pumps of the external type, as generally described in U.S. Pat. Nos. 4,562,751; 4,678,408; and 4,685,903; or automated implantable medication infusion pumps, as generally described in U.S. Pat. 4,573,994.

Relatively small and flexible electrochemical sensors have been developed for subcutaneous placement of sensor electrodes in direct contact with patient blood or other extracellular fluid, wherein such sensors can be used to obtain periodic readings over an extended period of time. In one form, flexible transcutaneous sensors are constructed in accordance with thin film mask techniques wherein an elongated sensor includes thin film conductive elements encased between flexible insulative layers of polyimide sheet or similar material. Such thin film sensors typically include exposed electrodes at a distal end for transcutaneous placement in direct contact with patient blood or the like, and exposed conductive contacts at an externally located proximal end for convenient electrical connection with a suitable monitor device. Such thin film sensors hold significant promise in patient monitoring applications, but unfortunately have been difficult to place transcutaneously with the sensor electrodes in direct contact with patient blood or other extracellular fluid. Improved thin film sensors and related insertion sets are described in commonly assigned copending U.S. Pat. Nos. 5,390,671; 5,391,250; and 5,482,473, which are incorporated by reference herein. See also U.S. Pat. No. 5,299,571.

The present invention relates specifically to an improved sensor insertion set adapted for quickly and easily placing a thin film sensor on a patient with sensor electrodes in direct contact with patient blood or other extracellular fluid.

SUMMARY OF THE INVENTION

In accordance with the invention, a subcutaneous insertion set is provided for placing a flexible sensor such as a thin film electrochemical sensor at a selected site within the body of a patient. The insertion set comprises a slotted insertion needle extending through a mounting base adapted for seated mounting onto the patient's skin. A flexible thin film sensor includes a proximal segment carried by the mounting base, and a distal segment protruding from the mounting base and having one or more sensor electrodes thereon. The distal segment of the sensor is carried within a protective cannula which extends from the mounting base with a portion of the cannula being slidably received within the insertion needle. One or more windows formed in the cannula are positioned in general alignment with the sensor electrodes on the sensor distal segment.

When the mounting base is pressed onto the patient's skin, the insertion needle pierces the skin to transcutaneously place the catheter with the sensor distal segment therein. The insertion needle can be withdrawn from the mounting base, leaving the catheter and sensor distal segment within the patient, with the sensors electrodes thereon exposed through the window or windows for direct contact with to patient fluid at the selected position within the patient, such as a subcutaneous, intravascular, intramuscular, or intravenous site. Conductive contacts on the sensor proximal end can be electrically connected to a suitable monitor device so that appropriate blood chemistry readings can be taken.

In the preferred form, the insertion needle has a cross-sectional shape which is somewhat greater than 180° in arcuate cross section. This part-circle needle construction protrudes downwardly from the mounting base of the insertion set, and terminates in a sharp tip for piercing the patient's skin. A first portion of the protective cannula has a cross sectional shape for nested reception within the insertion needle, to extend from the mounting base to a distal end which terminates at least slightly before the needle tip. This first portion of the cannula is sized for longitudinal sliding movement within the part-circle profile of the insertion needle, but to prevent lateral dislocation of the cannula from the insertion needle. A second portion of the cannula extends longitudinally in parallel with said first portion and defines a lumen for receiving and guidably supporting the distal end of the thin film sensor. At least one window is formed at or near the distal end of the lumen, in general alignment with the sensor electrodes, to expose said electrodes to patient body fluid. In the preferred form, the cannula is constructed from a resilient medical grade plastic or elastomer, and the second portion of the cannula cooperates with the insertion needle to define a substantially circular cross sectional shape for facilitated insertion into the patient's skin.

During insertion, the insertion needle and the protective cannula cooperatively protect and guide the sensor to the desired transcutaneous placement position. The insertion needle can then be withdrawn, whereupon the slotted needle geometry permits the insertion needle to slide over and longitudinally separate from the second portion of the cannula, thereby leaving the cannula and sensor therein at the selected insertion site.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view illustrating a transcutaneous sensor insertion set embodying the novel features of the invention;

FIG. 2 is an enlarged longitudinal vertical section taken generally on the line 2—2 of FIG. 1;

FIG. 3 is an enlarged longitudinal sectional of a slotted insertion needle used in the insertion set of FIGS. 1 and 2;

FIG. 4 is an enlarged transverse section taken generally on the line 4—4 of FIG. 3;

FIG. 5 is an enlarged transverse section taken generally on the line 5—5 of FIGS. 3;

FIG. 6 is an enlarged fragmented sectional view corresponding generally with the encircled region 6 of FIG. 2; and FIG. 7 is an enlarged transverse section taken generally on the line 7—7 of FIG. 2.

DETAILED DESCRIPTION OF THE PREFERRED EMBODIMENT

As shown in the exemplary drawings, an improved sensor insertion set referred to generally in FIG. 1 by the reference numeral 10 is provided for transcutaneous placement of a flexible sensor 12 (FIG. 2) at a selected site within the body of a patient. The insertion set 10 includes a rigid hollow slotted insertion needle 14 for quick and easy transcutaneous placement of a cannula 15 with a distal segment 16 of the sensor 12 therein, wherein the distal segment 16 has one or more sensor electrodes 18 exposed to patient fluid through a window 19 in the cannula 15. The insertion needle 14 is then withdrawable to leave the cannula 15 with the sensor distal segment 16 and the sensor electrodes 18 in place at the selected insertion site.

The transcutaneous sensor insertion set 10 of the present invention is particularly designed for facilitating accurate placement of a flexible thin film electrochemical sensor of the type used for monitoring specific blood parameters representative of patient condition. The insertion set 10 is designed to place the sensor subcutaneously or at another selected site within the body of a patient, in a manner minimizing patient discomfort and trauma. In one preferred application, the sensor 12 may be designed to monitor blood glucose levels, and may be used in conjunction with automated or semiautomated medication infusion pumps of the external or implantable type as described in U.S. Pat. Nos. 4,562,751; 4,678,408; 4,685,903 or 4,573,994, to deliver insulin to a diabetic patient.

In a preferred form, the flexible electrochemical sensor 12 is constructed according to so-called thin film mask techniques to include elongated thin film conductors embedded or encased between layers of a selected insulative material such as polyimide film or sheet. The sensor electrodes 18 (shown in exaggerated form in the drawings) at a tip end of the sensor distal segment 16 are exposed through one of the insulative layers for direct contact with patient blood, when the sensor is transcutaneously placed. The distal segment 16 is joined to a proximal segment 20, (FIG. 2) the end of which terminates in suitable conductive contact pads or the like which are also exposed through one of the insulative layers. As is known in the art, and illustrated schematically in FIG. 2, the proximal segment 20 and the contact pads thereon are adapted for electrical connection to a suitable monitor 22 for monitoring patient condition in response to signals derived from the sensor electrodes 18. Further description of flexible thin film sensors of this general type may be found in copending U.S. Pat. No. 5,482,473, entitled METHOD OF FABRICATING THIN FILM SENSORS which is incorporated by reference herein. The proximal segment 20 may be conveniently connected electrically to the monitor 22 by means of a connector block 24 as shown and described in copending U.S. Pat. No. 5,482,473, entitled FLEX CIRCUIT CONNECTOR, which is also incorporated by reference herein.

The sensor 12 is carried by a mounting base 26 adapted for placement onto the skin of a patient. As shown, the mounting base 26 comprises an enlarged and generally rectangular pad having an underside surface coated with a suitable pressure sensitive adhesive layer, with a peel-off paper strip 28 normally provided to cover and protect the adhesive layer, until the insertion set 10 is ready for use. As shown in FIGS. 1 and 2, the mounting base comprises upper and lower layers 30 and 32, with the proximal segment 20 of the flexible sensor 12 sandwiched therebetween. The proximal sensor segment 20 has a forwardmost end joined to the distal segment 16 which is folded angularly to extend downwardly through a slot 34 formed in the lower base layer 32.

The insertion needle 14 is adapted for slide-fit reception through a needle port 36 formed in the upper base layer 30 and further through the lower slot 34 in the lower base layer 32. As shown, the insertion needle 14 has a sharpened tip 38 and an open slot 40 which extends longitudinally from the tip 38 at the underside of the needle to a position at least within the slot 34 in the lower base layer 32. Above the mounting base 26, the insertion needle 14 may has a full round cross sectional shape and is desirably closed at a rear end thereof. In the preferred form, the slotted needle 14 has a part-circular cross sectional shape, with an arcuate dimension or span greater than 180°, such as on arcuate dimension of about 210°. This leaves a longitudinal slot in the needle with an arcuate dimension of about 150°.

The cannula 15 is shown best in FIGS. 6 and 7, and comprises a first portion 44 of part circular cross section fitted within the insertion needle 14 to extend downwardly from the mounting base 26. This cannula 15 is constructed from a suitable medical grade plastic or elastomer, such as polytetrafluoroethylene, silicone, etc., to define an open lumen 42 in a second portion thereof for receiving, protecting and guidably supporting the distal segment 16 of the sensor 12. The cannula 15 has one end fitted into the slot 34 formed in the lower layer 32 of the mounting base 26, wherein the cannula 15 is desirably secured to the mounting base by a suitable adhesive or other selected attachment means. From the mounting base 26, the cannula extends angularly downwardly with the first portion 44 nested within the insertion needle 14, terminating slightly before the needle tip 38. Importantly, at least one window 19 is formed in the lumen 42 near the distal end thereof, in general alignment with the sensor electrodes 18, to permit direct electrode exposure to patient body fluid when the sensor is transcutaneously placed.

In the preferred form, as shown in FIG. 7, the second portion 42 of the cannula 15 has a part-circular cross sectional shape which cooperates with the part-circular shape of the insertion needle 14 to define a substantially full-circle geometry for facilitated insertion through the patient's skin. The first portion 44 of the cannula 15 has a smaller cross sectional profile than the second portion 42, for sliding nested reception into the needle 14. The needle 14 and first cannula portion 44 are thus mechanically interlocked to prevent lateral dislocation of the cannula 15 from the insertion needle, while permitting longitudinal sliding motion of the needle over the cannula first portion 44. The distal or free end of the cannula second portion 42 is appropriately cut or otherwise set at an oblique angle, as viewed in FIG. 2, to form a continuation of the angle-cut tip 38 of the insertion needle.

In use, the insertion set 10 permits quick and easy transcutaneous placement of the sensor distal segment 16 at a selected site within the body of the patient. More specifically, the peel-off strip 28 (FIG. 1) is removed from the mounting base 26, at which time the mounting base 26 can be pressed onto and seated upon the patient's skin. During this step, the insertion needle 14 pierces the patient's skin and carries the protective cannula 15 with the sensor distal segment 16 therein to the appropriate transcutaneous placement site. During insertion, the cannula 15 provides a stable support and guide structure to carry the flexible sensor to the desired insertion site.

When the sensor 12 is transcutaneously placed, with the mounting base 26 seated upon the patient's skin, the insertion needle 14 can be slidably withdrawn from the patient. During this withdrawal step, the insertion needle 14 slides over the first portion 44 of the protective cannula 15, leaving the sensor distal segment 16 with electrodes 18 thereon at the selected insertion site. These electrodes 18 are directly exposed to patient body fluid via the window 19. The sensor proximal segment 20 is appropriately coupled to the monitor 32, so that the sensor 12 can then be used over a prolonged period of time for taking blood chemistry readings, such as blood glucose readings in a diabetic patient. If desired, the first portion 44 of the cannula 15 can be hollow as shown to form a second lumen available to deliver medication and/or sensor calibration fluid to the vicinity of the electrodes 18, or alternately to withdraw patient fluid such as blood for analysis.

The transcutaneous sensor insertion set of the present invention thus provides a relatively simple device for quickly and easily placing a flexible thin film electrochemical sensor at a selected position within a patient.

A variety of modifications and improvements to the transubcutaneous sensor insertion set of the present invention will be apparent to those skilled in the art. Accordingly, no limitation on the invention is intended by way of the foregoing description and accompanying drawings, except as set forth in the appended claims.

What is claimed is:

1. A transcutaneous sensor insertion set, comprising:
   a mounting base adapted for mounting onto a patient's skin;
   a flexible sensor having a proximal segment carried by said mounting base, and a distal segment protruding from said mounting base and having at least one sensor electrode thereon;
   a cannula protruding from said mounting base and having said sensor distal segment therein, said cannula defining at least one window disposed generally in alignment with said at least one sensor electrode on said sensor distal segment; and
   a hollow insertion needle carried by said mounting base to protrude therefrom and having at least a portion of said cannula nested therein, said insertion needle defining a longitudinally extending slot along one side thereof to permit sliding withdrawal of said needle from said mounting base and said nested portion of said cannula.

2. The transcutaneous sensor insertion set of claim 1 wherein said sensor is a flexible thin film sensor.

3. The transcutaneous sensor insertion set of claim 1 wherein said sensor is an electrochemical sensor.

4. The transcutaneous sensor insertion set of claim 1 wherein said sensor is a glucose sensor.

5. The transcutaneous sensor insertion set of claim 1 wherein said insertion needle extends through said mounting base, said insertion needle being manually withdrawable from said mounting base for separation from said nested portion of said cannula.

6. The transcutaneous sensor insertion set of claim 1 wherein said insertion needle is angularly carried by said mounting base, said slot in said insertion needle being formed in the side of the insertion needle presented away from said base.

7. The transcutaneous sensor insertion set of claim 1 wherein said cannula portion nested in said insertion needle comprises a first portion nested within said insertion needle, and said cannula further including a second portion defining a lumen with said sensor distal segment supported therein, said second portion having said at least one window formed therein.

8. The transcutaneous sensor insertion set of claim 7 wherein said insertion needle has a part-circular cross sectional shape with an arcuate dimension greater than 180°, said cannula first portion having a size and shape for longitudinal sliding movement of said needle and cannula first portion relative to each other but to prevent lateral dislocation of said cannula from said needle.

9. The transcutaneous sensor insertion set of claim 8 wherein said needle and said cannula second portion cooperatively define a substantially circular cross sectional shape when said cannula first portion is nested within said needle.

10. The transcutaneous sensor insertion set of claim 1 including means for connecting said sensor proximal segment to a monitor.

11. The transcutaneous sensor insertion set of claim 1 wherein said mounting base includes means for removable attachment thereof to a patient's skin.

12. A transcutaneous sensor insertion set, comprising:
    a mounting base adapted for mounting onto a patient's skin;
    a flexible sensor having a proximal segment carried by said mounting base, and a distal segment protruding from said mounting base and having at least one sensor electrode thereon;
    a cannula protruding from said mounting base, said cannula defining a first portion and a second portion extending generally in parallel to each other, said second cannula portion defining a lumen with said sensor distal segment received and supported therein, said second cannula portion further defining at least one window disposed generally in alignment with said at least one sensor electrode on said sensor distal segment, and
    a hollow insertion needle carried by said mounting base to protrude therefrom, said insertion needle having a part-circular cross sectional shape with an arcuate dimension greater than 180° thereby defining a longitudinal slot with an arcuate dimension less than 180°, said cannula first portion having a size and shape for nested and longitudinally slidable reception within said insertion needle, whereby said insertion needle pierces a patient's skin upon placement of said mounting base onto the patient's skin, said needle carrying said cannula with said sensor distal segment therein to a selected insertion site, said needle being slidably withdrawable from said cannula and said mounting base to leave said cannula with said sensor distal segment therein at the selected insertion site.

13. The transcutaneous sensor insertion set of claim 12 wherein said sensor is a flexible thin film sensor.

14. The transcutaneous sensor insertion set of claim 12 wherein said insertion needle forms an acute angle with said mounting base, said slot in said insertion needle being formed in the side of the insertion needle presented away from said base.

15. The transcutaneous sensor insertion set of claim 12 wherein said cannula first portion has a size and shape for longitudinal sliding movement of said needle and cannula first portion relative to each other but to prevent lateral dislocation of said cannula from said needle.

16. The transcutaneous sensor insertion set of claim 15 wherein said needle and said cannula second portion cooperatively define a substantially circular cross sectional shape when said cannula first portion is nested within said needle.

17. A transcutaneous insertion set, comprising:

a mounting base adapted for mounting onto a patient's skin;

a cannula protruding from said mounting base; and a hollow insertion needle carried by said mounting base to protrude therefrom and having at least a portion of said cannula nested therein, said insertion needle defining a longitudinally extending slot along one side thereof to permit sliding withdrawal of said needle from said mounting base and said nested portion of said cannula;

said insertion needle having a cross sectional shape with an arcuate dimension greater than 180 degrees to prevent lateral dislocation of said nested cannula portion from said needle while permitting longitudinal sliding movement of said needle and cannula relative to each other.

18. The transcutaneous insertion set of claim 17 wherein said insertion needle extends through said mounting base, said insertion needle being manually withdrawable from said mounting base for separation from said nested portion of said cannula.

19. The transcutaneous insertion set of claim 17 wherein said insertion needle forms an acute angle with said mounting base, said slot in said insertion needle being formed in the side of the insertion needle presented away from said base.

20. The transcutaneous insertion set of claim 17 wherein said cannula portion nested in said insertion needle comprises a first portion nested within said insertion needle, and said cannula further including a second portion defining a lumen.

21. The transcutaneous insertion set of claim 20 wherein said needle and said cannula second portion cooperatively define a substantially circular cross sectional shape when said cannula first portion is nested within said needle.

* * * * *